United States Patent [19]
Keyser

[11] Patent Number: 5,510,544
[45] Date of Patent: Apr. 23, 1996

[54] FLUORINATED TERPENE COMPOUNDS

[75] Inventor: Gene E. Keyser, Jacksonville, Fla.

[73] Assignee: Environmental Solvents Corporation, Jacksonville, Fla.

[21] Appl. No.: 101,361

[22] Filed: Aug. 2, 1993

[51] Int. Cl.$^6$ .................. C07C 19/08; C07C 25/13
[52] U.S. Cl. .................. 570/125; 570/136; 252/89.1; 252/162; 252/173; 252/546; 134/40
[58] Field of Search ............... 252/558, 559, 252/171, 173, 89.1, 162; 510/127, 136

[56] References Cited

U.S. PATENT DOCUMENTS

| | | | |
|---|---|---|---|
| T947,009 | 6/1976 | Ammons | 156/344 |
| 2,438,038 | 3/1948 | Craver | 252/170 |
| 4,113,435 | 9/1978 | Lagow et al. | 422/191 |
| 4,120,810 | 10/1978 | Palmer | 252/153 |
| 4,143,079 | 3/1979 | Moore | 260/648 |
| 4,414,128 | 11/1983 | Goffinet | 252/111 |
| 4,576,738 | 3/1986 | Colodney et al. | 252/559 |
| 4,659,498 | 4/1987 | Stoufer | 252/153 |
| 4,740,247 | 4/1988 | Hayes et al. | 134/42 |
| 4,790,951 | 12/1988 | Frieser et al. | 252/162 |
| 5,112,358 | 5/1992 | Deal, III | 8/137 |
| 5,243,094 | 9/1993 | Borg | 568/822 |
| 5,250,208 | 10/1993 | Merchant et al. | 252/67 |
| 5,300,154 | 4/1994 | Ferber et al. | 134/26 |
| 5,362,919 | 11/1994 | Costello et al. | 568/601 |

FOREIGN PATENT DOCUMENTS 60-32723  2/1985  Japan .

OTHER PUBLICATIONS

Harada et al, CA 104: 50631, "2,6–dihaloalalkyl benzenes . . .", 1985, (corresponding to JP 60152429) (Abst. Only).
Weichert et al, CA 68:86772, "Preparation of alkyl fluorides . . ." 1968, Z. Chem, 8(2), 64–5 (Abstract Only).
Bergmann et al, CA 55:23436, "2,3–Difluorostyrene . . . ", J. Org. Chem., 26, 919–23 (1961) (Abstract Only).
The Merck Index, 10th Edition, pp. 397, 907, Merck & Co. Inc. Rahway N.J. 1983.
Rozen et al., *Synthesis*, Jun./Jul. 1985 at 665.
Gal et al., 25 *Tetrahedron Letters* 449 (1984).
Gal et al., 26 *Tetrahedron Letters* 2793 (1985).
Rozen et al., 50 *J. Org. Chem.* 3342 (1985).
Rozen et al., 16 *Journal of Fluorine Chemistry* 19 (1980).
Wiggins, "The Synthesis Of Fluorinated Terpenes And The Mechanism Of Farnesyl Pyrophosphate Synthetase," University of Utah Ph.D. Thesis dated Aug. 1980.

*Primary Examiner*—Allen J. Robinson
*Assistant Examiner*—Brian G. Bembenizk
*Attorney, Agent, or Firm*—Cesari and McKenna

[57] ABSTRACT

Fluorinated terpenes useful in a wide variety of general cleaning and degreasing applications are disclosed. These compounds have high solvencies but reduced flash points, and include derivatives of paracymene and myrcene, both of which, while relatively unreactive, are nonetheless miscible with a wide variety of hydrocarbon soils. The compounds exhibit flash points of 25° F. or more above those of the unmodified terpenes.

12 Claims, No Drawings

FLUORINATED TERPENE COMPOUNDS

BACKGROUND OF THE INVENTION

1. Field of the Invention

The present invention relates to terpene compounds, and specifically to fluorinated terpenes useful in a wide variety of general cleaning and degreasing applications.

2. Description of the Related Art

Useful industrial cleaning solvents and compositions must typically satisfy a host of demanding criteria for effectiveness. Most commercial applications involve removal of grease or other petroleum derivatives, necessitating favorable chemical interaction between the solvent and the material to be removed; therefore, the solvent is typically itself a hydrocarbon or derivative thereof. In addition, to provide a reasonable shelf life, the solvent should remain stable over a long period of time and through the temperature fluctuations ordinarily associated with commercial storage and/or use. General-purpose cleaners should also be environmentally and toxicologically benign.

Various terpenes have recently been identified as highly useful cleaners. By and large this class of hydrocarbon compound exhibits superior solvency characteristics and is readily available and inexpensive, fully biodegradable, and non-toxic. Terpenes have been employed, for example, in hot- and cold-tank degreasing operations, metal-parts cleaning, electrical-parts cleaning, adhesive-removal, and ink-removal applications.

Because terpenes are hydrocarbons, however, their flash points rarely exceed about 120° F. That limitation can prove problematic in cleaning contexts that involve exposing soiled articles to relatively high temperatures, since safety considerations dictate temperatures of use well below a solvent's flash point. Typical high-temperature applications of cleaning solvents include vapor-phase exposure and azeotropic processes, in which the cleaning solvent is combined and evaporated with a second solvent and/or liquid-phase contaminants.

DESCRIPTION OF THE INVENTION

Objects of the Invention

It is, therefore, an object of the present invention to provide terpene compounds having flash points higher than those associated with unmodified hydrocarbon terpenes.

It is another object of the invention to provide novel and versatile cleaning compositions for use in a variety of cleaning processes.

It is a further object of the invention to obtain high-flash-point terpene compounds that are stable and environmentally benign.

Other objects will, in part, be obvious and will, in part, appear hereinafter. The invention accordingly comprises the compositions, features, and combinations of elements, that will be exemplified in the following description, and the scope of the invention will be indicated in the claims.

Detailed Description of the Preferred Embodiments

I have found that controlled fluorination of certain terpene compounds results in significant elevation of their flash points. That increase is enough to permit safe use of cleaning compositions containing these compounds at higher process temperatures and in cleaning systems otherwise incompatible with terpene properties. Furthermore, the fluorinated compounds of the present invention exhibit satisfactory stability properties while retaining the advantageous environmental and toxicity characteristics associated with unmodified terpenes.

The fluorinated terpenes of the present invention are derivatives of paracymene and myrcene, both of which, while relatively unreactive, are nonetheless miscible with a wide variety of hydrocarbon soils. These compounds exhibit flash points of 25° F. or more above those of the unmodified terpene compounds. Their structural formulas are as follows:

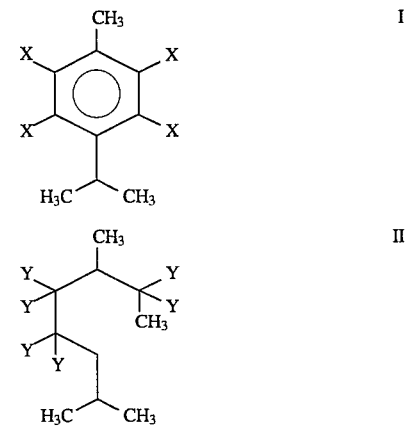

In Compound I, derived from paracymene (p-isopropyl-toluene), X denotes either hydrogen or fluorine; fluorine replacement can therefore occur at any of the unsubstituted phenyl positions. Compound I can include as few as two and up to four fluorine atoms. While the difluorocymene embodiment of Compound I performs advantageously, the tri- and tetrafluorcymene embodiments are particularly preferred for their higher flash points.

In compound II, derived from myrcene (2-methyl-6-methylene- 2,7-octadiene), Y denotes either hydrogen or fluorine; fluorine replacement can therefore occur at the unsubstituted methylene groups. Compound II can include as few as two and up to eight fluorine atoms.

Either compound can be combined with one or more emulsifiers and/or wetting agents (hereafter referred to collectively as surfactants), which may be anionic, cationic, or nonionic in nature. These materials are frequently added, for example, to solvent compositions that are rinsed off with water. In addition, provision of a surfactant can improve the efficacy of a solvent in removing various types of soil. Generally, combination of the fluorinated terpene compound with up to 10%, by weight, of the surfactant is preferred.

Surfactants suitable for use with the fluorinated compounds of the present invention include salts of higher alkylaryl sulfonates, including alkali-metal and amine salts of dodecyl benzene sulfonic acid; salts of tall-oil fatty acids, including alkali-metal and amine salts; condensates of hydrophobic moieties with polymer lower alkylene oxides; and mixtures of the foregoing.

Alternatively or in addition to use of a surfactant, residual terpene solvent can be removed by contacting the cleaned article at an elevated temperature with one or more additional solvents either by dilution or to form an azeotropic solvent combination. In the latter case the combination is ordinarily evaporated azeotropically, and the additional solvent or solvents should therefore exhibit relatively low boiling points and volatilities higher than those of the terpene solvent. In general, they should boil at a temperature below the azeotroping temperature to ensure complete removal during evaporation.

The preferred azeotroping solvent is water, alone or in combination with aliphatic compounds such as ketones, amines, ethers or alcohols. Preferred aliphatic compounds contain less than 8 (desirably 1–4) carbon atoms. Particularly preferred materials are propanols and butanols such as isopropanol and isobutanol.

C. WORKING EXAMPLES

Example 1

Fluorination of Paracymene

In a Teflon-lined reactor were combined 25 ml paracymene, 25 ml CFCl$_3$, and 3 ml of 1M BCl$_3$ in CH$_2$Cl$_2$. Fluorine gas, diluted with nitrogen gas to a concentration of 5% as a safety precaution, was provided to the reactor through a sodium fluoride trap. BCl$_3$ in CH$_2$Cl$_2$ serves as a Lewis acid catalyst to promote aromatic addition products; the sodium fluoride trap was utilized to ensure removal of unwanted water vapor and/or hydrogen fluoride.

Exit gases were collected and passed through a sodium iodide trap containing 1% sodium iodide dissolved in water. Fluorine addition was continued at a rate of approximately 1 ml/sec until the sodium iodide trap turned brown, indicating the presence of unreacted fluorine gas. At this point $^{19}$F NMR spectroscopy revealed multiple resonances indicative of more than one monofluorinated material and a difluorinated material. GC/MS analysis confirmed the presence of unreacted paracymene, two monofluorinated derivatives, one difluorinated species, and some higher-boiling fluorinated residues. The fluorine was incorporated in the derivatives on the aromatic nucleus.

The material was purified by combining the products of several runs, each performed as described above, and vacuum distilling the non-residue products. The crude distillate was reacted with bromine and the majority of the previously unreacted paracymene removed by subsequent distillation. Fluorinated derivatives were not separately isolated.

The mixture was found have a boiling point of about 203° F. at about 15 mm Hg. Its flash point was about 137°–138° F., which is approximately 20° F. higher than unmodified paracymene. The GC/MS analysis indicates that the finally distilled material includes the monofluoroparacymenes 2- and 3-fluoroisopropyltoluene; a single difluoroparacymene that is either 2,6- or 2,5-difluoro-4-isopropyltoluene; and residual paracymene in an overall ratio of 15:53:8. The finally distilled mixture was found to be stable to heat, air, and water.

Further reaction would be expected to produce more highly fluorinated end products.

Example 2

Fluorination of Myrcene

Using the configuration described in Example 1, a reactor containing 0.5 ml myrcene in 25 ml CFCl$_3$ was provided with fluorine (5% in nitrogen) gas through a sodium fluoride trap at approximately 1 ml/sec until the exit gases turned a sodium iodide trap brown, indicating the presence of unreacted fluorine gas. Following fluorination, $^{19}$F NMR spectroscopy revealed multiple resonances indicative of more than one monofluorinated material and a difluorinated material. GC/MS analysis confirmed the presence of unreacted myrcene, two monofluorinated derivatives, and one difluorinated species. The mixture slowly evolved hydrogen fluoride upon standing, indicating the presence of one or more unstable components.

Further reaction would be expected to produce more highly fluorinated and stable end products.

It will therefore be seen that the present invention provides partially fluorinated terpene compositions that may be used to great advantage in industrial cleaning applications. The terms and expressions which have been employed are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A cleaning composition comprising a fluorinated terpene compound of the formula:

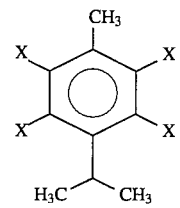

wherein X is hydrogen or fluorine and at least two of X are fluorine.

2. A cleaning composition comprising a fluorinated terpene compound of the formula:

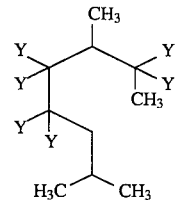

wherein Y is hydrogen or fluorine and at least two of Y are fluorine.

3. The cleaning composition of claim 1 further comprising a surfactant.

4. The cleaning composition of claim 3 wherein the proportion of surfactant does not exceed 10 wt %.

5. The cleaning composition of claim 2 further comprising a surfactant.

6. The cleaning composition of claim 5 wherein the proportion of surfactant does not exceed 10 wt %.

7. The cleaning composition of claim 1 further comprising an azeotropic solvent.

8. The cleaning composition of claim 7 wherein the azeotropic solvent includes water.

9. The cleaning composition of claim 8 wherein the azeotropic solvent further includes an aliphatic compound.

10. The cleaning composition of claim 2 further comprising an azeotropic solvent.

11. The cleaning composition of claim 10 wherein the azeotropic solvent includes water.

12. The cleaning composition of claim 11 wherein the azeotropic solvent further includes an aliphatic compound.

* * * * *